United States Patent
Eriksson et al.

(10) Patent No.: US 12,409,342 B2
(45) Date of Patent: Sep. 9, 2025

(54) IMAGING SYSTEM FOR A RADIOTHERAPY DEVICE

(71) Applicant: Elekta Limited, Crawley (GB)

(72) Inventors: Markus Eriksson, Crawley (GB); Per Carlsson, Gustavsberg (SE); Stefan Langemark, Crawley (GB)

(73) Assignee: Elekta Limited, Crawley (GB)

( * ) Notice: Subject to any disclaimer, the term of this patent is extended or adjusted under 35 U.S.C. 154(b) by 164 days.

(21) Appl. No.: 18/003,809

(22) PCT Filed: Jun. 30, 2021

(86) PCT No.: PCT/EP2021/068046
§ 371 (c)(1),
(2) Date: Dec. 29, 2022

(87) PCT Pub. No.: WO2022/003046
PCT Pub. Date: Jan. 6, 2022

(65) Prior Publication Data
US 2023/0248999 A1   Aug. 10, 2023

(30) Foreign Application Priority Data

Jul. 1, 2020 (GB) ........................... 2010083
Feb. 5, 2021 (GB) ........................... 2101643

(51) Int. Cl.
*A61N 5/10* (2006.01)
*A61B 6/00* (2006.01)
(Continued)

(52) U.S. Cl.
CPC ............ *A61N 5/1049* (2013.01); *A61B 6/032* (2013.01); *A61B 6/06* (2013.01); *A61B 6/4078* (2013.01);
(Continued)

(58) Field of Classification Search
CPC ...... A61N 5/10; A61N 5/1049; A61N 5/1077; A61N 2005/1054; A61N 2005/1061;
(Continued)

(56) References Cited

U.S. PATENT DOCUMENTS

| 5,548,627 A | 8/1996 | Swerdloff et al. |
| 2002/0071517 A1 | 6/2002 | Hoffman |

(Continued)

FOREIGN PATENT DOCUMENTS

| CN | 1723853 | 1/2006 |
| CN | 101961530 A | 2/2011 |

(Continued)

OTHER PUBLICATIONS

"International Application Serial No. PCT/EP2021/068046, International Search Report dated Sep. 28, 2021", (Sep. 28, 2021), 6 pgs.

(Continued)

*Primary Examiner* — Jurie Yun
(74) *Attorney, Agent, or Firm* — Schwegman Lundberg & Woessner, P.A.

(57) ABSTRACT

Disclosed herein is a radiotherapy device comprising a source of therapeutic radiation and an imaging system, the imaging system comprising a source of imaging radiation and a detector. The imaging system is switchable between a first configuration and a second configuration wherein, in the first configuration, the imaging system is configured to emit a beam of imaging radiation shaped for a first imaging modality toward the detector and, in the second configuration, the imaging system is configured to emit a beam of imaging radiation shaped for a second imaging modality toward the detector. The detector is of a shape formed by at least a first and a second section, the first and second section intersecting one another, wherein the first section is positioned for receiving the beam of imaging radiation for the (Continued)

first imaging modality, and the second section is positioned for receiving the beam of imaging radiation for the second imaging modality.

19 Claims, 5 Drawing Sheets

(51) Int. Cl.
    *A61B 6/03*   (2006.01)
    *A61B 6/06*   (2006.01)
    *A61B 6/40*   (2024.01)
    *A61B 6/42*   (2024.01)

(52) U.S. Cl.
    CPC .......... *A61B 6/4085* (2013.01); *A61B 6/4233* (2013.01); *A61B 6/4266* (2013.01); *A61B 6/4452* (2013.01); *A61N 5/1077* (2013.01); *A61N 2005/1054* (2013.01); *A61N 2005/1061* (2013.01)

(58) Field of Classification Search
    CPC .. A61N 2005/1089; A61B 6/032; A61B 6/06; A61B 6/4078; A61B 6/4085; A61B 6/4233; A61B 6/4266; A61B 6/4452
    See application file for complete search history.

(56) References Cited

U.S. PATENT DOCUMENTS

| | | |
|---|---|---|
| 2009/0283682 A1 | 11/2009 | Star-lack et al. |
| 2011/0096894 A1 | 4/2011 | Uehara et al. |
| 2015/0131774 A1 | 5/2015 | Maurer, Jr. et al. |
| 2018/0243585 A1 | 8/2018 | Lachaine et al. |
| 2020/0121267 A1 | 4/2020 | Deutschmann |
| 2020/0171328 A1 | 6/2020 | Shea et al. |

FOREIGN PATENT DOCUMENTS

| | | |
|---|---|---|
| CN | 108969906 A | 12/2018 |
| EP | 0948930 A1 | 10/1999 |
| EP | 2383702 A1 | 11/2011 |
| WO | WO-2010136911 A1 | 12/2010 |
| WO | WO-2016030772 A1 | 3/2016 |

OTHER PUBLICATIONS

"International Application Serial No. PCT/EP2021/068046, Written Opinion dated Sep. 28, 2021", (Sep. 28, 2021), 6 pgs.
"United Kingdom Application Serial No. 2010083.0, Examination Report dated Dec. 22, 2020", (Dec. 22, 2020), 5 pgs.
"United Kingdom Application Serial No. 2101643.1, Examination Report dated Jul. 7, 2021", (Jul. 7, 2021), 10 pgs.
"European Application No. 21 736 329.0, Examination Report dated Mar. 11, 2025", (Mar. 11, 2025), 9 pgs.
"Chinese Application No. 202180058178.X, Office Action dated Jul. 10, 2025", w English Translation, (Jul. 10, 2025), 13 pgs.

IMAGING SYSTEM FOR A RADIOTHERAPY DEVICE

PRIORITY APPLICATIONS

This application is a U.S. National Stage Filing under 35 U.S.C. § 371 from International Application No. PCT/EP2021/068046, filed on Jun. 30, 2021, and published as WO2022/003046 on Jan. 6, 2022, which claims the benefit of priority to United Kingdom Application No. 2101643.1, filed on Feb. 5, 2021, and to United Kingdom Application No. 2010083.0, filed on Jul. 1, 2020; the benefit of priority of each of which is hereby claimed herein, and which applications and publication are hereby incorporated herein by reference in their entireties.

This disclosure relates to an imaging system for a radiotherapy device and methods therefor.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour. However, in order to apply a prescribed dose to a tumour or other target region within a subject, the radiation must pass through healthy tissue, irradiating and hence potentially damaging it in the process. It is a general aim of the field to minimise the dose received by healthy tissue during radiotherapy treatments. Many different radiotherapy techniques exist, allowing radiation to be applied from different angles, at varying intensities, and for specific time periods.

Before radiotherapy treatment, a radiation therapy treatment plan is created to determine how and where the radiation should be applied. Typically, such a treatment plan is created with the assistance of medical imaging technology. For example, a computed tomography (CT) scan may be taken of the patient in order to produce a three-dimensional image of the area to be treated. The three-dimensional image allows the treatment planner to observe and analyse the target region and identify surrounding tissues. In addition, a series of three-dimensional images can be recorded over a period of time, such as a breathing cycle, in order to provide a four-dimensional (4DCT) video that can inform the treatment plan. Typically, these images are acquired using a dedicated imaging device such as a CT scanner.

Known imaging systems include CT imaging systems and cone beam computed tomography (CBCT) imaging systems. CT imaging systems have various advantages and disadvantages compared to CBCT imaging systems, with differences in quality, physical size, time of measurement, and cost.

When designing a CT imaging system, it is generally desirable to provide a large CT imaging panel in order to collect more imaging radiation attenuation data as the gantry of the imaging device rotates. This can increase imaging speed and thus improve patient throughput. The accuracy of the measurements can also be increased by using a larger detector.

So-called 'tileable' photodetectors are a new innovation in the field of dedicated CT scanners. These tileable detectors are each capable of creating an independent signal indicative of the intensity of imaging radiation incident thereon. These detectors can be stacked or 'tiled' together to create a photodetector panel of a custom size. The resulting detector panel can be described as an array of photodetectors, and in particular an array of photodetectors each capable of producing a signal indicative of the intensity of imaging radiation incident thereon and of communicating the signal to a processor. These detector arrays allow images with an increased image size with an improved resolution to be generated.

Radiotherapy devices may also comprise imaging systems. Such devices allow the patient to be imaged on the day of treatment, for example to ensure their anatomy is properly aligned with the anatomy shown in the images forming the basis of the treatment plan. Images may also be taking during treatment to improve the precision and accuracy of the treatment.

Typically, radiotherapy devices do not incorporate CT imaging systems. To date, radiotherapy devices have instead used CBCT imaging systems. In part, this is because CBCT imaging is quicker, and imparts a lower radiation dose to the patient. The considerations for designing a CBCT imaging system are different to the considerations when designing a CT imaging system. For example, in CBCT imagers, clinicians may desire to image small, high contrast objects such as stent placements or, small cracks in spines. For radiotherapy, CBCT imaging of bone/soft tissue boundary and air/soft tissue is used as a surrogate for the position of organs in the patients. Therefore, what has so far driven the CBCT market and innovation in the field of imaging systems for radiotherapy devices is to have smaller and smaller pixels to better resolve these anatomical features. It is generally preferable that a detector for a CBCT system should be as small as possible. This is in contrast to the general aim when designing a CT imaging system: to provide a CT panel which is as large as possible given cost and space constraints.

As with CT imaging systems, to date, tileable detectors have also been thought unsuitable for use in a radiotherapy environment. In part, this is because it has been thought that the advantages provided by tileable detectors are applicable only for CT systems, rather than the CBCT systems traditionally used with radiotherapy devices. Also, while the tileable photodetectors are designed to withstand damage caused by incident imaging radiation, for example X-rays at an energy suitable for imaging, they are not designed to withstand damage caused by much more intense incident radiation, for example from a source of therapeutic radiation in a radiotherapy device.

The present application seeks to improve upon these and other disadvantages encountered in the prior art.

SUMMARY

An invention is set out in the independent claims. Optional features are set out in the dependent claims.

Embodiments will now be described, by way of example, with reference to the drawings of which:

DETAILED DESCRIPTION

Figure 1:
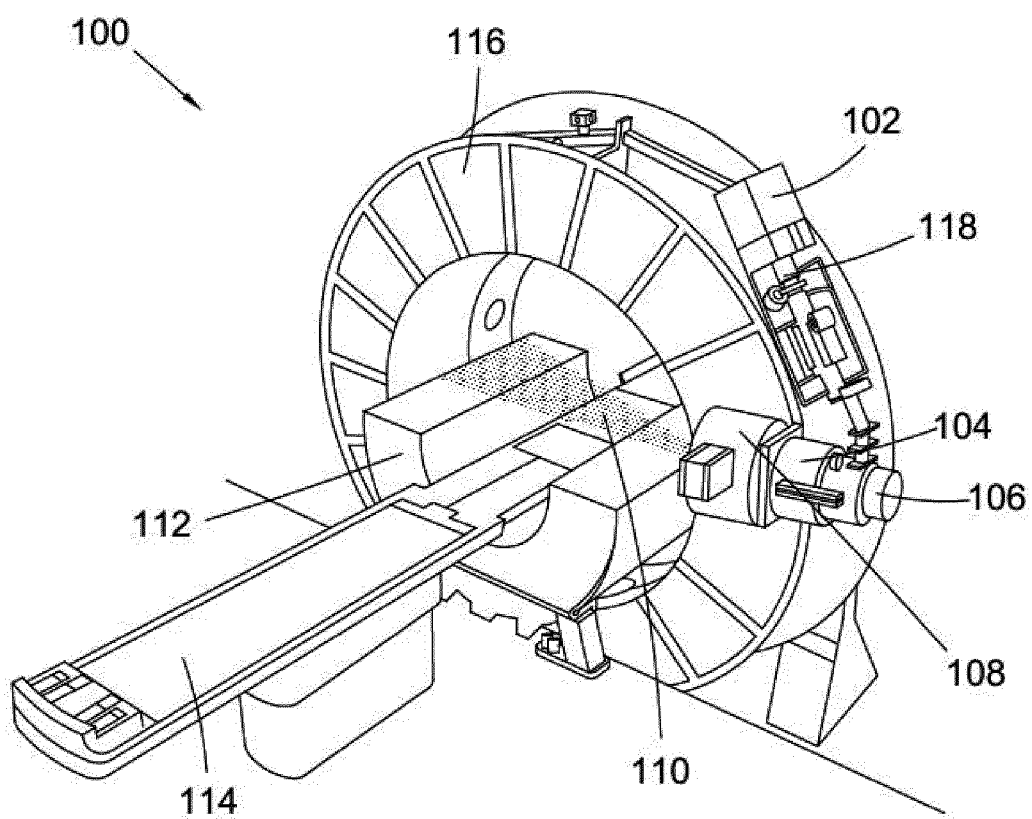
FIG. 1 shows a radiotherapy device or apparatus of known type.

In overview, the present disclosure relates to an imaging system for a radiotherapy device that can provide both CT imaging capability and CBCT imaging capability. In some implementations, the imaging system comprises a single source of imaging radiation, and a single detector. Implementations are disclosed in which the single common source of imaging radiation can be used to provide alternate imaging modalities, representing alternately CT imaging capability and CBCT imaging capability, by switching between them. The single detector is of a shape formed by at least a first and a second section, the first and second section intersecting one another, wherein the first section is positioned for receiving the beam of imaging radiation for a first imaging modality and the second section is positioned for receiving the beam of imaging radiation for a second imaging modality.

It is desirable to have a radiotherapy device that is equipped with both CT and CBCT capabilities in order to make use of the advantages of both techniques. There are many challenges involved with providing such systems as part of a radiotherapy device, including complexity and cost.

Disclosed herein is a radiotherapy device configured to provide therapeutic radiation to a patient, the device comprising a source of therapeutic radiation and an imaging system. The imaging system comprises a source of imaging radiation and a detector. The detector comprises an array of tileable photodetectors, each configured to provide a signal indicative of the intensity of imaging radiation incident thereon.

The imaging system is suitable for use either as a CT imaging system or a CBCT imaging system, with each technique making use of a single common detector and a single common source.

As used herein, a CT imaging system is distinguished from a CBCT imaging system. These terms are used to refer to different imaging modalities and different associated imaging devices. CT imaging involves rotating a source of imaging radiation 360° around a patient at axially spaced positions with a fan beam directed towards a relatively narrow panel in order to acquire data which can be used to produce a 2D cross-sectional image of the patient. Either the source of imaging radiation, or the patient, can then be incrementally advanced in order to acquire another 2D image and thereby build up a 3D image of the patent or region of interest via multiple 360° rotations around the patient. Alternatively, rather than incremental advancements, the patient or source of radiation can be advanced slowly and continuously while the radiation source rotates, in order to acquire the necessary data to construct a 3D CT image via a spiral or helical delivery of imaging radiation. In a 'true' or 'traditional' CT imager, the imaging radiation is typically emitted in a thin 'fan' shape that projects an elongated shape that is much narrower in one direction than the other onto the detector. Hence a narrow, curved detector is used.

In contrast, a CBCT imaging system uses a broader, cone-shaped beam and larger panel in order to cover a large volume of the patient with a single full or half or other angle of rotation around the patient, thereby acquiring multiple 2D projections of the object from various angles used to reconstruct a 3D image, and CBCT systems are therefore able to provide 3D images quickly and with a reduced number of gantry rotations in comparison to traditional CT systems. For example, it is possible to achieve a 3D imaging volume via a single 180 degree rotation around a patient using a CBCT modality.

A CT detector is typically very expensive per unit area and so the surface area is minimised by using a curved detector that is translated around a patient. The curvature follows the geometry and angular spread of the fan beam and can have a comparatively narrow dimension transverse to the plane of the beam, i.e., of dimension comparable to the fan beam thickness. CBCT images are obtained using a normally less expensive two-dimensional flat panel detector that is not of sufficient quality to be used for CT imaging due to several technical differences and drawbacks. The CBCT images are typically quicker to obtain than CT images, and are typically used for intrafraction imaging. In part due to these advantages of cost and speed, CBCT imaging systems have been considered for use with radiotherapy devices, for example to provide 3D images which may guide or form the basis of radiation therapy.

However, CBCT images are typically lower quality and, unlike images produced by spiral delivery CT imaging, CBCT images contain inherent artefacts that need to be accounted for. Those disadvantages might compromise 3D image quality obtained by a CBCT system. There are other advantages achieved by using a thinner slice with spiral imaging in CT, such as that the scatter to the panel is reduced and, as mentioned above, the reconstruction process produces fewer artefacts—in general a higher image quality and lower dose to the patient can be obtained by CT imaging. However, a radiotherapy device comprising a 'true' or 'traditional' CT imaging system, capable of providing higher quality imaging than CBCT, is difficult to develop due to the cost and complexity of such a system. Even when trying to integrate a CT imaging system into a radiotherapy device, it is desirable to also include a CBCT-type imaging technique based on a two-dimensional panel, particularly for intrafraction imaging. However, producing such a large area panel with the quality required additionally for a CT imaging functionality is expensive.

Accordingly, disclosed herein is an imaging system that can be integrated with a radiotherapy device in order to provide multiple types, or modalities, of imaging. The disclosure enables CT imaging and CBCT imaging to be integrated into a radiotherapy device without significant cost or complexity increase and with minimal change in the dimensions of the device. Furthermore, the integrated device may benefit from a simplified wiring and interconnection configuration.

Although this disclosure describes various examples and embodiments relating to CBCT imaging, it should be understood that the systems, devices, and methods disclosed herein may in fact be used to perform other types of cross-sectional imaging, including 2D imaging and 3D imaging. Accordingly, apparatus described as suitable for CBCT, such as detectors, should be interpreted as being suitable for the desired cone beam imaging technique, i.e. it may not be necessary for the detector to enable a full 3D sample to be produced and it may instead be designed to produce a 2D CBCT-type image. Similarly, variations of 3D and 4D CT imaging exist and the use of the term 'CT' should not be taken to be limiting to one particular variation of a 2D-slice or spiral configuration. The disclosure is intended to relate to a higher quality form of pre-treatment imaging, referred to as 'CT', and a lower quality, but faster, form of intrafraction imaging, referred to as 'CBCT'.

FIG. 1 shows a radiotherapy (RT) device 100. The device and its constituent components will be well known to the skilled person but is described here generally for the purpose of providing useful accompanying information for the present disclosure.

The RT device 100 shown in FIG. 1 comprises a source 102 of radiofrequency waves, RF transmission apparatus 103, an accelerating waveguide 104, a source of electrons 106, a treatment head including a collimator 108 such as a multi-leaf collimator used to shape a treatment beam 110, housing 112 (shown partially cut away), and a patient support surface 114. The depicted device does not have the usual housing which would cover the entire RT apparatus in a commercial setting such as a hospital. In use, the device would also comprise the housing which, together with the ring-shaped gantry, defines a bore. The patient support surface 114 is moveable and can be used to support a patient and move them, or another subject, into the bore when radiotherapy is to commence.

The RT apparatus beam generation system comprises the source 102 of radiofrequency waves, the accelerating waveguide 104, and the source of electrons 106. The beam generation system is configured to produce a beam of radiation, otherwise known as the treatment beam 110, that is collimated and shaped by the collimator 108 and directed towards the bore. The beam generation system is based on a linear accelerator (linac) design.

The source 102 of radiofrequency waves, such as a magnetron, is configured to produce radiofrequency waves. The source 102 of radiofrequency waves is coupled to the accelerating waveguide 104 via the RF transmission apparatus 103, which may include a circulator, and is configured to pulse radiofrequency waves into the accelerating waveguide 104. Radiofrequency waves may pass from the source 102 of radiofrequency waves through an RF input window and into an RF input connecting pipe or tube. The source of electrons 106, such as a diode or triode electron gun, is also coupled to the accelerating waveguide 104 and is configured to inject electrons into the waveguide 104. The injection of electrons into the accelerating waveguide 104 is synchronised with the pumping of the radiofrequency waves into the accelerating waveguide 104. The design and operation of the source 102 of radiofrequency waves, source of electrons 106, and the accelerating waveguide 104 is such that the radiofrequency waves accelerate the electrons to very high energies as the electrons propagate through the accelerating waveguide 104.

The design of the accelerating waveguide 104 depends on whether the accelerating waveguide 104 accelerates the electrons using a standing wave or travelling wave, though the waveguide typically comprises a series of cells, each cell connected by a hole or 'iris' through which the electron beam may pass. The cells are coupled in order that a suitable electric field pattern is produced which accelerates electrons propagating through the accelerating waveguide 104. As the electrons are accelerated in the accelerating waveguide 104, the electron beam path may be controlled by a suitable arrangement of steering magnets, or steering coils, which surround the accelerating waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the accelerating waveguide 104 is evacuated using a vacuum system comprising a vacuum pump or an arrangement of vacuum pumps. The pump system is capable of producing ultra-high vacuum (UHV) conditions in the accelerating waveguide 104. The vacuum system also ensures UHV conditions in the source of electrons 106 and, if used, the drift tube and flight tube. Electrons can be accelerated to speeds approaching the speed of light in the evacuated waveguide.

The beam generation system is configured to direct the treatment beam 110 toward a patient positioned on the patient support surface 114. The treatment beam 110 comprises therapeutic radiation. The beam generation system may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce the treatment beam 110. The X-rays may be filtered and may pass through one or more ion chambers for dose measuring. The beam can be shaped in various ways by beam-shaping apparatus, for example by using the collimator 108, before it passes into the patient as part of radiotherapy treatment.

In some implementations, the beam generation system is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the beam generation system. In essence, it is possible to swap between the first and second mode by moving the heavy metal target in or out of the electron beam path and replacing it with a so-called 'electron window'. The electron window is substantially transparent to electrons and allows electrons to exit the flight tube.

Typically, a radiation detector is positioned diametrically opposed to the collimator 108. The radiation detector is suitable for, and configured to, produce radiation intensity data. In particular, the radiation detector is positioned and configured to detect the intensity of radiation which has passed through the subject. The radiation detector may form part of a portal imaging system.

The beam generation system is attached to the rotatable gantry 116 so as to rotate with the gantry 116. In this way, the beam generation system is rotatable around the patient so that the treatment beam 110 can be applied from different angles around the gantry 116. In a preferred implementation, the gantry is continuously rotatable. In other words, the gantry can be rotated by 360 degrees around the patient, and in fact may continue to be rotated past 360 degrees. The gantry may be ring-shaped, i.e. a ring-gantry.

The RT device 100 of FIG. 1 may be controlled by a controller (not shown). The controller is a computer, processor, or other processing apparatus. The controller may be formed by several discrete processors; for example, an RT apparatus processor, which controls the operation of the RT apparatus; and a subject support surface processor which controls the operation and actuation of the patient support surface 114. The controller is communicatively coupled to a memory, e.g. a computer readable medium.

Figure 2A:
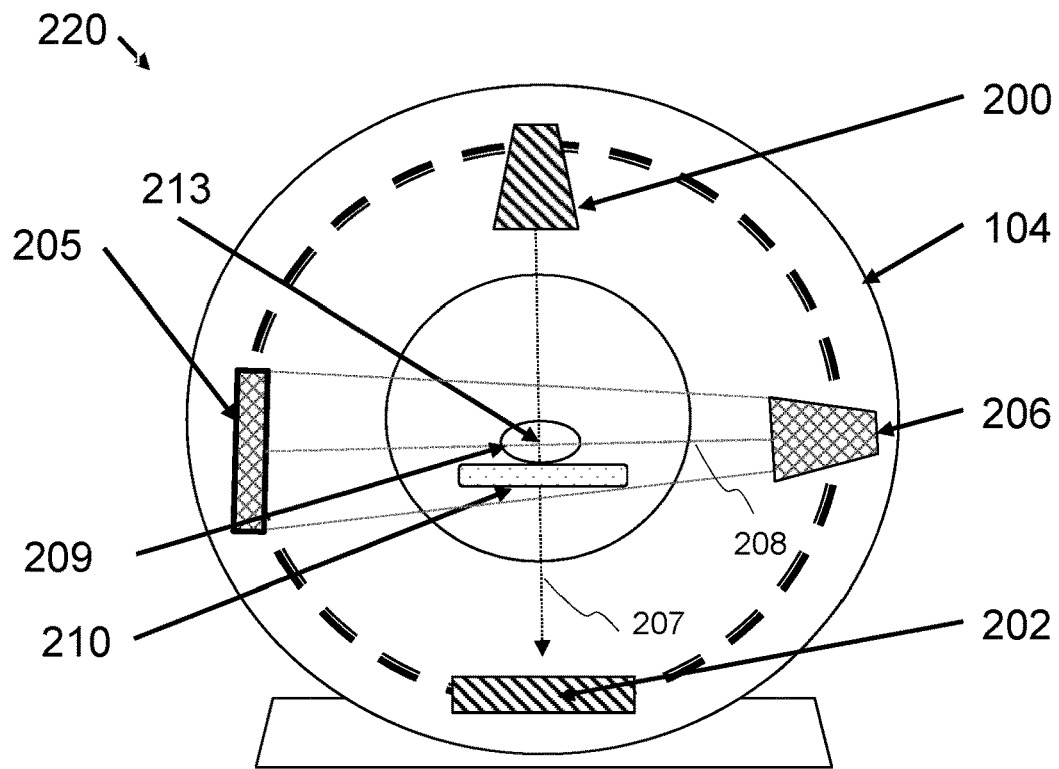
FIG. 2a shows a cross-sectional view of a radiotherapy device or apparatus of known type with an imaging system.
Figure 2B:
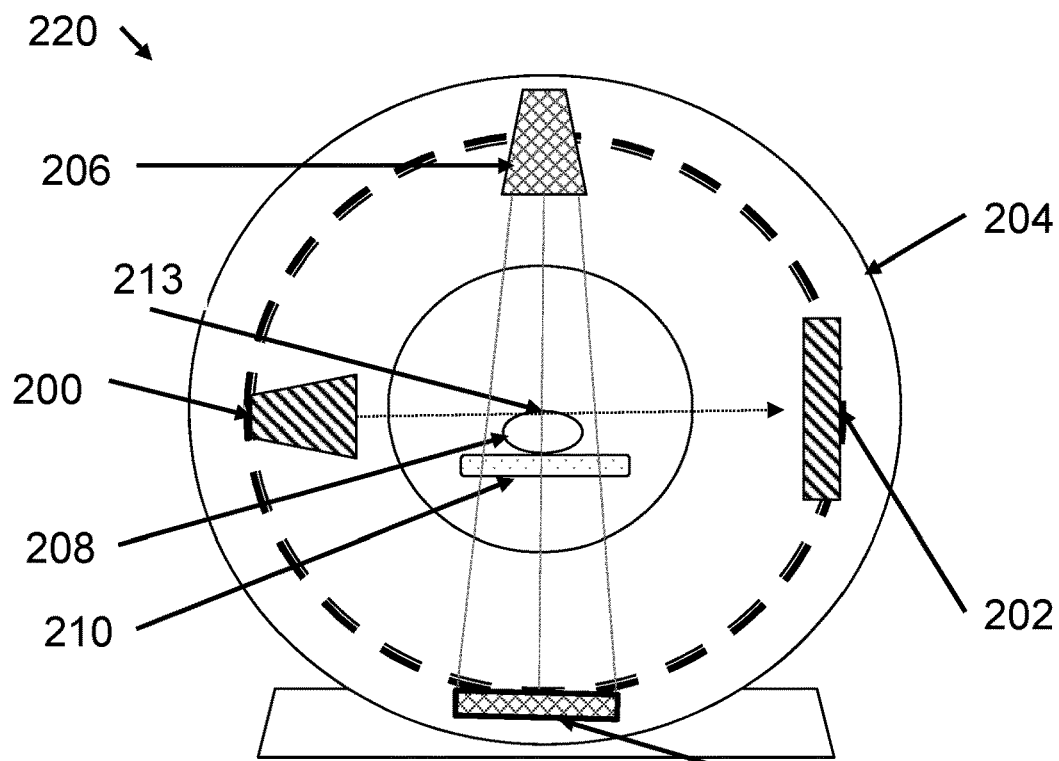
FIG. 2b shows a cross-sectional view of a radiotherapy device or apparatus of known type with an imaging system.

FIG. 2a and FIG. 2b show a possible geometrical arrangement of a radiotherapy device 220, which may be the radiotherapy device 100 of FIG. 1, that additionally comprises an imaging system of known type, such as a CBCT imaging system. The imaging system comprises a source of imaging radiation 206, such as a source of X-ray radiation, and an imaging detector 205. The device 220 depicted in FIGS. 2a and 2b is configured to provide radiotherapy treatment in a co-planar arrangement. The imaging system and source of therapeutic radiation 200 are coupled to a gantry 204, which may be a ring gantry. The source of therapeutic radiation 200 is configured to emit radiation along a therapeutic radiation axis 207 to a radiation detector 202 and the source of imaging radiation 206 is configured to emit radiation along an imaging beam axis 208.

The source of therapeutic radiation 200 is rotatable around a patient 209 positioned in a treatment volume of the device 220. The point in space through which the therapeutic radiation axis 207 passes regardless of gantry rotation angle is the radiation isocentre 213. In other words, radiation may be delivered to a radiation isocentre 213 at the centre of the gantry 204 regardless of the angle to which the radiation head 200 is rotated around the gantry 204. The rotation axis of the gantry 204 may also pass through the radiation isocentre 213, in a direction which is perpendicular to both the therapeutic radiation axis 207 and the imaging radiation axis 208. In the co-planar arrangement depicted in FIGS. 2a and 2b, radiation is emitted in a plane which is perpendicular to the axis of rotation of the radiation source 200.

The device 220 may comprise a moveable patient table 210 which is configured to move the patient 213 into, and out from, the bore of the gantry 204. The patient table 210 may be moveable by a suitable arrangement or configuration of motors and actuators. To provide an image of the patient 213, the patient table 213 is actuated to move the patient into the bore of the gantry. While at least a portion of the patient 213 is inside the bore, the imaging system rotates around the patient while the source of imaging radiation 206 emits a beam of radiation. Radiation intensity data is collected by the detector 205, which is indicative of the degree to which the imaging radiation has been attenuated by the patient 213.

As the radiation is delivered to the patient, for example according to a treatment plan, the gantry 204 rotates causing the radiation detector 202 and source of therapeutic radiation 200 to rotate together around the circular support track 206 such that they are always arranged 180 degrees from one another around the gantry 204. The source of therapeutic radiation 200 thus directs radiation toward the patient 209 from various angles around the patient 209. In FIG. 2a, the source of therapeutic radiation 200 is at the top of the gantry 204 and the radiation detector 202 is at the bottom of the gantry 204. FIG. 2b shows both components having been rotated 180 degrees about the gantry rotation axis, which is into the plane of the diagram.

The components of the imaging system and the radiotherapy system can be rigidly coupled to the gantry 204 so as to retain a fixed angle, which can be 90 degrees or another value, between each component as the gantry 204 is rotated. In FIG. 2a, the source 206 of imaging radiation is at the right-hand side of the gantry 204 and the imaging radiation detector 205 is at the left-hand side of the gantry 204. FIG. 2b shows both components having been rotated 180 degrees about the gantry rotation axis. The angle between the therapeutic radiation beam axis and imaging radiation axis is constant and independent of the rotation of the gantry.

The geometry of FIG. 2a and FIG. 2b may be used alternatively for either CT imaging or CBCT imaging. For CT imaging, an appropriate CT imaging detector and CT source of imaging radiation are used. FIG. 2a and FIG. 2b show a fan beam of imaging radiation, as would be used for CT imaging. In that case, the source of imaging radiation 206 is configured to emit a fan-shaped beam which nonetheless has a central axis which is depicted in the figures as a dashed line. As will be familiar to those skilled in the art, a fan-shaped beam, or fan beam, is a beam with a cross-section having a narrow beamwidth in one dimension and a wider beamwidth in the other dimension. For CBCT imaging, a respective CBCT imaging radiation detector and source of imaging radiation are used. In that case, the source of imaging radiation 206 is configured to emit a cone-shaped beam. Unlike the fan-shaped beam, a cone-shaped beam, or cone beam, has a cross-section having a similar beamwidth in each dimension. The gantry can be rotated such that the source of imaging radiation 206 and the imaging radiation detector 205 rotate about the patient according to the position and speed requirements necessary to produce the desired image. As the imaging system is rotated and attenuation data is gathered, data from different angles is collected which allows the reconstruction of a cross-sectional image using known techniques. The imaging system may also comprise a processor, or controller, configured to receive signals from each of the detectors and produce, or reconstruct, an image based on the signals.

Figure 3:
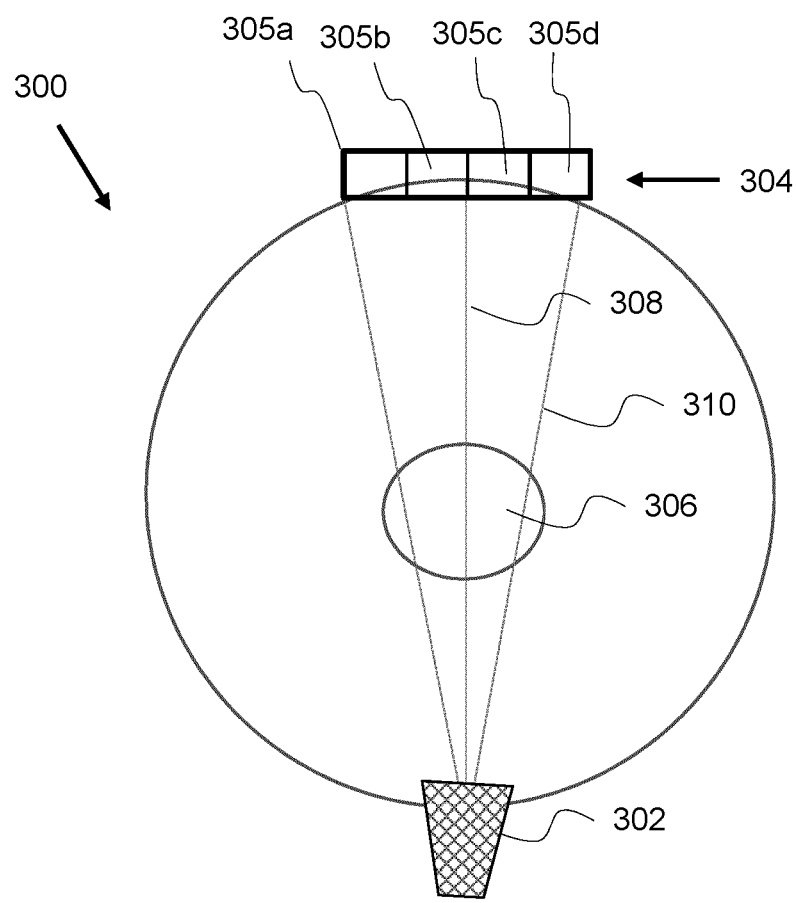
FIG. 3 shows a schematic of a device comprising a detector with tileable photodetectors according to the present disclosure.

FIG. 3 depicts a schematic of an imaging system 300 for a radiotherapy device that makes use of the tileable photodetectors. Although only imaging components are shown in FIG. 3, the system 300 may be used in place of the imaging system of the radiotherapy device 220 of FIG. 2a and FIG. 2b and hence each of the components of FIG. 3 may be mounted on a gantry like that of FIG. 2a and FIG. 2b and may be rotatable about a patient. In particular, the gantry may be a ring gantry and further, the gantry may be continuously rotatable. The imaging system comprises a source 302 of imaging radiation and a detector panel 304. The detector panel 304 comprises an array of tileable photodetectors 305a-d.

Each individual photodetector 305a-d is configured to provide a signal indicative of the intensity of imaging radiation incident thereon.

Each tile may comprise a sensor such as a direct conversion compound semiconductor sensor, a processor such as a readout integrated circuit (IC) and, optionally a substrate. The sensor is configured to convert CT energy photons, such as x-ray or gamma ray photons, into detectable electronic currents. In other words, the detector panel 304 may function as a CT detector.

The source 302 is configured to be switchable between at least two configurations. In a first configuration suitable for a first imaging modality, such as CT imaging, the source is configured to emit a fan-shaped beam of imaging radiation 310 having a centre-line 308. In a second configuration suitable for a second imaging modality, such as CBCT imaging, the source is configured to emit a cone beam of radiation along the same axis as the centre-line 308. The source 302 may be switched between different configurations and hence between different imaging modalities by using a collimator component. For example, two different collimators may be provided to the source, one suitable for producing a fan beam and the other suitable for producing a cone beam. The appropriate collimator can be moved in and out of the beam path as required in order to produce the desired beam. Alternatively, a single, reconfigurable collimator may be used with the source 302. Imaging radiation can be passed through a patient 306 located in the treatment volume to obtain CT slice data or CBCT data. The source 302 of imaging radiation may be rotated 360 degrees completely around the patient in order to obtain slice data from a range of angles in order to provide a 3D image.

The imaging system may also comprise a processor, or controller, configured to receive the signals from each of the tileable detectors and produce, or reconstruct, a CT image or CBCT image based on the signals.

The array of tileable detectors may be located, arranged and/or positioned at a particular position around the gantry. For example, the detector panel may be located at 45 degrees from the therapeutic radiation source. In such an implementation, i.e. in which the separation between the therapeutic radiation beam stop and the imaging panel 105 is increased, the imaging panel may be protected from damage caused by the high intensity radiotherapy radiation.

In examples that make use of a gantry, a source of therapeutic radiation and the source 302 of imaging radiation may be positioned on the gantry such that the source of therapeutic radiation is configured to emit radiation along a first axis and the source 302 of imaging radiation is configured to emit radiation along a second axis; wherein the first and second axes meet at a point which defines a common isocentre for the source of therapeutic radiation and the imaging system 300. The detector panel 304 may hence be positioned to receive imaging radiation that is emitted along the second axis. Furthermore, the rotation axis of the gantry may pass through the common isocentre, in a direction which is perpendicular to both beam axes.

Disclosed herein is a radiotherapy device configured to provide therapeutic radiation to a patient, the device comprising a source of therapeutic radiation and an imaging system; wherein the imaging system comprises a source of imaging radiation and a detector, the detector comprising an array of tileable photodetectors each configured to provide a signal indicative of the intensity of imaging radiation incident thereon.

Figure 4A:
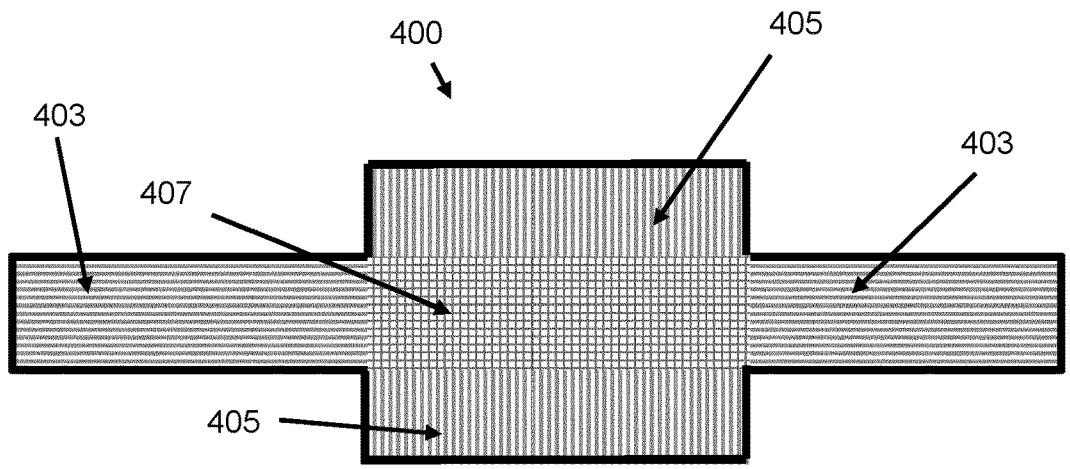
FIG. 4A shows a cross-sectional view of a detector according to the present disclosure.

FIG. 4A shows a cross section of an example detector panel 400 that can be used to incorporate two different imaging modalities, for example CT imaging and CBCT imaging, within one system, rather than having to limit a system to a single imaging modality due to cost and complexity constraints. The detector panel 400 is viewed from above, with imaging radiation being incident into the page. The detector panel 400 is made up of tileable photodetectors and may be used as the detector panel 304 of FIG. 3. The detector 400 comprises a first section, 403 and a second section 405. The sections may be referred to as areas, or portions, of the detector 400. In FIG. 4A, the first section 403 is depicted using horizontal shading, while the second section 405 is depicted using vertical shading. There is an intersection area 407 that is an area common to both the first section 403 and the second section 405. The intersection area 407 is marked by a hatched (or a 'crossed') shading pattern in FIG. 4A.

The first section 403 of the detector is shaped and positioned for receiving a beam of imaging radiation shaped for a first imaging modality. In the implementation depicted in FIG. 4A, the first section 403 is long and rectangular and thus is shaped to receive a fan-shaped beam from an imaging system. In other words, the first section 403 has a shape which substantially matches the cross-sectional shape of the CT imaging beam. Such a beam of radiation may be compatible with, for example, CT imaging. The second section 405 of the detector is shaped and positioned for receiving a beam of imaging radiation shaped for a second imaging modality. In the implementation depicted in FIG. 4A, the second section 405 is substantially square-shaped, though in some implementations the second section may be circular or substantially circular in shape. Thus, the second section is shaped to receive a beam with a circular cross-section, e.g. from an imaging system according to a CBCT image modality. In other words, the second section 405 has a shape which substantially matches the cross-sectional shape of the CBCT imaging beam.

The intersection area 407 can be considered as an area of overlap between the first section 403 and the second section 405. The intersection area 407 can also be considered to lie within the perimeter of both of the first section 403 and the second section 405. However, the two sections do not entirely overlap, and neither does any section lie entirely within the other. The intersection area 407 advantageously allows a detector with reduced surface area to be used even when providing multiple imaging modalities, which would conventionally require multiple detectors.

Each of the first and second sections is formed of tileable photodetectors of a nature and quality suitable for CT imaging. For example, the tiles may be solid-state detectors comprising a scintillator and/or photodetector. The first and second sections thus define the shape, or profile, of the face of the detector panel 400. In particular, the outer perimeters of the first and second sections define the perimeter and hence shape of the detector panel 400.

The first section 403 has a slim, elongated face that has a length equivalent to the lateral body width of a patient in the direction of which a cross-sectional image is to be obtained (in one example, the standard length of 80 cm is used). The width of the face of the first section 403 does not extend further than is necessary in order to provide measurements suitable for CT imaging, reducing the total detector surface area required. The first section 403 of the detector panel 400 can thus be used to detect the wide, fan beam used in CT techniques and which can be provided by the source 302 of FIG. 3. In an example, the dimensions of the first section 403 are 800 mm×64 mm, although any suitable size may be used.

The two sections may also be referred to as limbs of the detector. The second section 405 has an area that is differently shaped to the first section 403, with a width and length that are more similar in size to each other and less elongated than the first section 403, and may in fact produce a square shaped area, or even a circle-shaped area. In some examples, the first section 403 and the second section 405 overlap such that the overall profile of the detector resembles a cross shape, as shown in FIG. 4A.

Figure 4B:
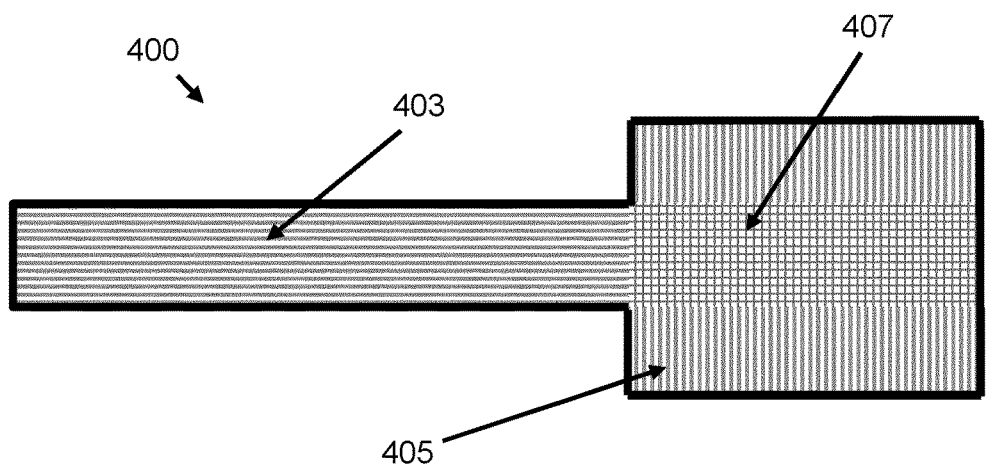
FIG. 4B shows a cross-sectional view of a detector according to the present disclosure.
Figure 4C:
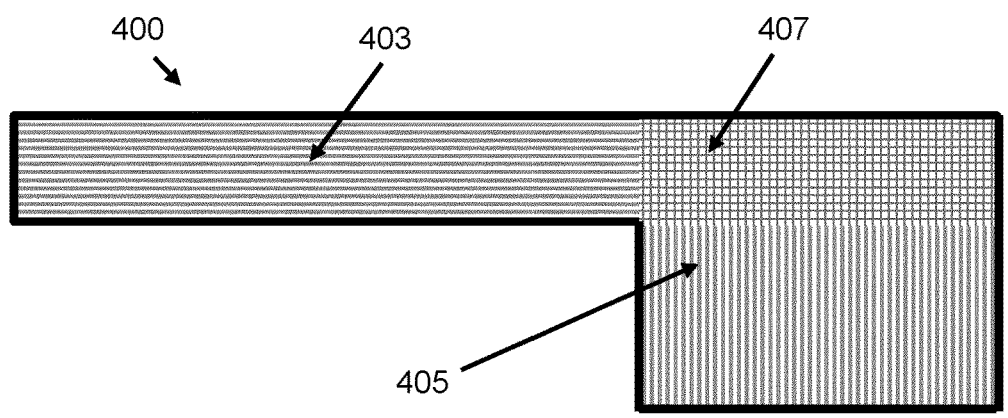
FIG. 4C shows a cross-sectional view of a detector according to the present disclosure.

Alternatively, the first section 403 and the second section 405 overlap such that the overall profile of the detector resembles the shape of a letter 'T' or the shape of a letter 'L', as shown in FIG. 4B and 4C respectively. For example, as shown in FIG. 4B, the detector panel 400 is arranged to have a 'T' shape, having a second section 405 which is quadrilateral in shape and a first section 403 which is an elongated limb that extends therefrom. The first section 403 may be sized like that of the example of FIG. 4A in order to enable CT imaging. FIG. 4C shows a further example arrangement in which a quadrilateral second section 405 is positioned at one end of a first section 403 but is off-centre when compared to the example of FIG. 4B, producing an 'L' shape rather than a 'T' shape.

Like the example of FIG. 4A, an intersection area 407 is depicted on FIG. 4B and FIG. 4C that is common to each of the respective first section 403 and the second section 405. Each of these possible shapes or profiles is suitable for use within the systems and methods of the present disclosure. In each example, the second section 405 can hence be used for imaging techniques using a broader, cone-shaped beam, such as CBCT, advantageously using the tileable CT photodetectors to provide superior quality than is usually associated with CBCT imaging while retaining the faster imaging time of a CBCT technique.

The two intersecting sections create a detector panel that, in one example, has a cross-shaped overall profile, or perimeter. Whether a cross-shape, T-shape, L-shape, or other arrangement is used, the overall shape of the detector panel 400 is not rectangular, and can be described as a non-quadrilateral shape, or a shape with more than four vertices.

Such a detector panel 400 can be used with the switchable source 302 of FIG. 3. such that a radiotherapy device containing a single imaging source and a single imaging detector can provide multiple imaging techniques, such as CT imaging and CBCT imaging, wherein CT imaging is used as a first imaging modality and CBCT imaging is used as a second imaging modality In one example, when the imaging source 302 is in the first configuration and emits a fan-shaped beam, or fan beam, of imaging radiation, the imaging radiation illuminates the first section 403 of the detector panel 400. When the imaging source 302 is in the second configuration and emits a cone-shaped beam, or cone beam, of imaging radiation, the imaging radiation illuminates the second section 405 of the detector panel 400.

The area covered by the first section 403 may be curved, with the axis of curvature being the same as the axis of curvature of the gantry, although the degree of curvature may not be the same. The second section 405 may be curved likewise, or, alternatively, one or both sections may be flat. The detector panel 400 may therefore be a planar detector or a curved detector, or a partly planar or partly curved detector, depending upon the desired application. In some examples, the degree of curvature or flatness is the same for the second section 405 as for the first section 403.

The detector panel 400 is sized such that it advantageously does not extend the length of the bore of the radiotherapy device, which is determined by other parts and components of the gantry. Thus, respective detection capability suitable for CT imaging and CBCT imaging can be achieved without unduly increasing the size or footprint of the radiotherapy device. Furthermore, the system can enable CT imaging while utilising an existing radiotherapy device gantry that can rotate for example at 20 rpm, or even faster, without requiring modification to the gantry structure or driving technique, producing very high cost efficiency.

The source 302 of imaging radiation and detector is rotated about the subject according to the requirements of a CT imaging technique (using the first section 403) or a CBCT imaging technique (using the second section 405).

The imaging coordinate systems of the respective CBCT and CT imaging are very accurately calibrated with reference to the radiation isocentre 213. Hence the images acquired and the 3D volumes reconstructed can be related to the radiation isocentre 213 so that the patient offset can be calculated and compensated for.

In some examples, the source 302 of imaging radiation is configured to move such that two alternative collimators can be used. In examples wherein the overlapping intersection area 407 of the first section 403 and the second section 405 is offset from the centre of the overall detector length, thus producing a detector with an overall 'T-shape' or 'L-shape' profile, the source 302 of imaging radiation may be configured to move such that it can be directed to illuminate either the length of the first section 403 or the length of the second section 405. Alternatively, an adjustable collimator mounted to the source 302 of imaging radiation may be used to produce the same effect. Alternatively, a single adjustable collimator is used. The purpose of each collimator component is to shape the beam appropriately for the respective technique of CT or CBCT, i.e. a fan-beam of imaging radiation is produced for a CT technique that is to be detected using the first section 403 of the detector panel 400, and a cone beam of imaging radiation is produced for a CBCT technique that is to be detected using the second section 405. Alternatively, a single collimator component may be used that is adjustable such that it either produces a fan beam or a cone beam. In each example, the fan beam has a cross section that is much narrower in one dimension that the other, and the cone beam has a cross section that has two similar dimensions, and may be approximately circular or square. In one example, rather than moving the source 302 of imaging radiation either laterally or angularly, the source 302 of imaging radiation emits a wide enough cone or fan beam that both detector sections are illuminated by it. In such an example, collimation may be selectively applied such that a cone beam is incident on the second section 405 for CBCT and a fan beam is incident on the first section 403 for CT. Such an approach is dependent upon enough flux density being provided by the wider beam that each detector can obtain adequate signal.

In some examples, the source 302 of imaging radiation is an x-ray tube and generator suitable for CT imaging, although other forms of imaging radiation may be used. Using the same source for two types of imaging beneficially allows both types of imaging to be integrated into a radiotherapy system without undue cost and complexity. CT imaging can be used for pre-treatment imaging and CBCT, or 2D, imaging can be used for intrafraction imaging. When using an x-ray tube and generator, the generator is configured such that the source 302 of imaging radiation can be operated either in a pulsed manner or in a continuous manner. In either pulsed or continuous operation, the source may illuminate either one detector section at a time, or both panels simultaneously, depending upon the arrangement and method chosen from those disclosed herein. The source may operate at a typical energy of between 50 to 150 kV but may also operate outside of that range, or at more than one energy.

In some examples, the source 302 of imaging radiation is selected and positioned so that its field of view barely projects onto the full surface of the second section 405 of the detector panel 400, in other words, such that the second section 405 substantially fills the imaging source field of view. A control system of the source 302 of imaging radiation is configured so that the source can operate in a pulsed manner and/or can operate in a manner suitable for fluoroscopy, with continuous beams of imaging radiation.

In some examples, a source of therapeutic radiation and a source of imaging radiation may be positioned on the gantry such that the source of therapeutic radiation is configured to emit radiation along a first axis and the source of imaging radiation is configured to emit radiation along a second axis; wherein the first and second axes meet at a point which defines a common isocentre for the source of therapeutic radiation and the imaging system. The detector panel 400 may hence be positioned to receive imaging radiation that is emitted along the second axis in each of the first and second imaging modalities. Furthermore, the rotation axis of the gantry may pass through the common isocentre, in a direction which is perpendicular to both beam axes.

The present disclosure therefore allows detector surface area, and the associated high expense, to be reduced in comparison with a large surface area CT detector. A further advantage of the detector panel 400 of FIG. 4A is that the source 302 of imaging radiation need not be physically moved in order for the system to alternate between CT and CBCT imaging, instead, the collimation of the imaging radiation is changed in order to fit the appropriate detection shape for the desired technique.

Figure 5:
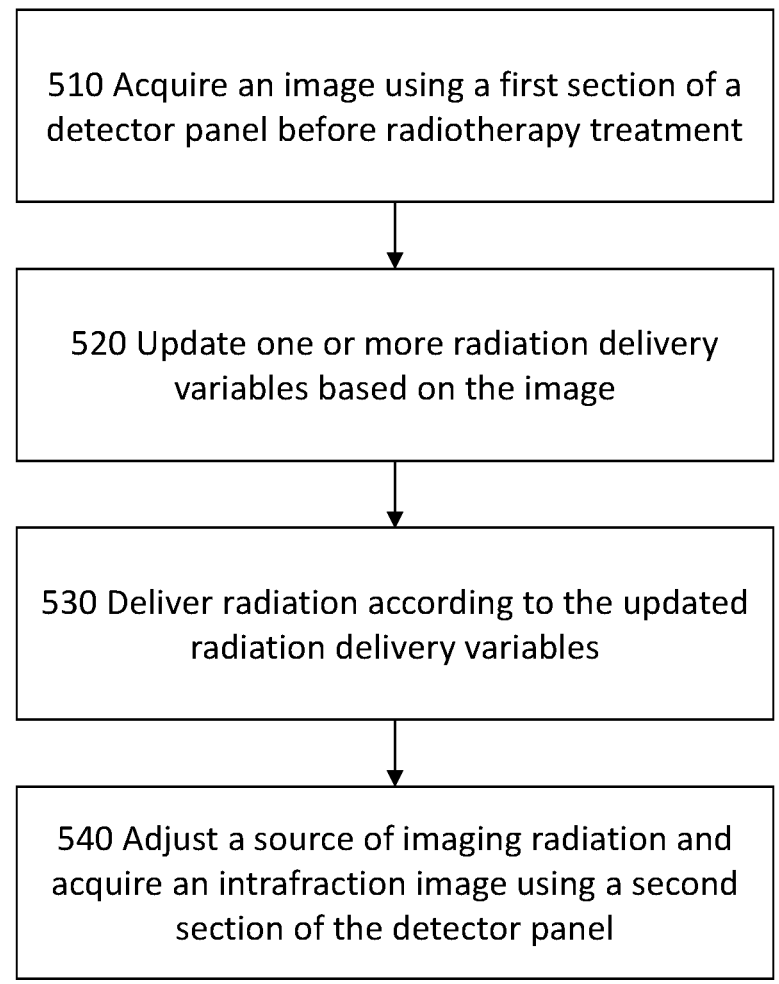
FIG. 5 shows steps performed in a method for radiotherapy imaging according to the present disclosure.

FIG. 5 is a flowchart depicting a method 500 according to the present disclosure. The method 500 may be performed using any of the systems depicted in FIG. 3, FIG. 4A, FIG. 4B, or FIG. 4C. The method 500 is an example of the improved imaging options allowed by the systems of the present disclosure.

In overview, the method 500 may be used to update an existing treatment plan during delivery of the plan, i.e. during the radiotherapy treatment. An image taken by an imaging system at a particular gantry rotation angle and along a particular 'line of sight' can be used to inform the delivery of radiation along the same line of sight.

In an example, an existing treatment plan may be comprised of a set of several radiation delivery variables which have been determined for each of a plurality of gantry rotation angles. Clinical equivalent CT images can be taken and a 3D tomographic volume reconstructed. The original plan can thus be checked against the actual anatomy of the patient and, if needed, the plan can be updated or adapted so that the plan and dose to be delivered will accurately hit the target from all angles. Alternatively, the position of the patient can be adjusted in 3D or in 6D according to the CT image(s). Such pre-treatment imaging can be performed using the CT imaging capability of the system.

At step 510, the source of imaging radiation is in a first configuration and a first imaging modality is used to acquire an image using a first section of a detector panel. In an implementation, the first imaging modality is CT imaging, and the image is a CT image. The first section of the detector panel is suitable for CT imaging, such as the first section 403 of the detector panel 400 of FIG. 4A.

As described above, the source of imaging radiation is adjustable, switchable, or configurable, or produces a sufficiently wide beam, such that it can illuminate the detector with a fan beam and a cone beam as required. At step 510, the source of imaging radiation is configured such that it can illuminate the first section of the detector panel.

At step 520, one or more therapeutic radiation delivery variables are generated, or updated, based on the acquired image. This can be done in any appropriate manner as will be apparent to the skilled reader. For example, the radiation delivery variables may include one or more therapeutic radiation beam weights. The radiation delivery variables may also include beam collimation variables, which may relate to the shape and size of the beam of therapeutic radiation. Beam collimation variables may include, for example, the position of one or more leaves of a multi-leaf collimator (MLC), the position of a beam blocker or beam diaphragm, and/or the degree of tilt or the position of the beam source, a beam blocker and/or MLC. The radiation delivery variables may also include the length of time for which therapeutic radiation is delivered. The radiation delivery variables may also include a gating variable, which determine whether or not the beam is gated, i.e. halted.

In an example, the CT image shows that the target region has changed position relative to the images which were used to form the basis of the original treatment plan. This may be because the tumour has grown or shrunk since that time, and/or because the patient is in a different position on the support surface of the radiotherapy device. The radiation delivery variables can be updated to account for this change. For example, the MLC leaf positions may be adjusted, either systematically or individually, in order that the desired dose distribution is achieved, the patient positioning system can be adjusted in 3D or in 6D or the treatment plan can be updated—all to achieve target coverage and spare healthy tissue. The update can be performed using known optimisation techniques which are known to the skilled person. It will be appreciated by those skilled in the art that in some examples, step 520 is optional and may not be necessary, dependent upon whether or not the results of the CT image show that it is necessary update the radiation delivery variables.

At step 530, the gantry is rotated so that the therapeutic radiation beam axis aligns with the imaging beam axis at the time the image was acquired at point 520. In other words, the image is acquired at a first time along a first axis. The gantry is rotated by the necessary angle until, at a second time, the radiation beam axis aligns with the first axis such that the source of therapeutic radiation can deliver therapeutic radiation along the first axis.

At step 540, radiation is delivered according to the updated radiation delivery variable. The source of imaging radiation is adjusted, either by changing its angle or tilt, or moving it laterally, or adjusting a collimator, such that it is switched to a second configuration for performing a second imaging modality and is able to illuminate a second section of the detector panel. The second section of the detector panel is suitable for 2D or CBCT imaging, such as the second section 405 of the detector panel 400 of FIG. 4A, and is used to perform intrafraction imaging, hence the second imaging modality may be CBCT imaging and a CBCT image may be acquired. The second section of the detector panel may intersect, or partially overlap with, the first section of the detector panel but neither section entirely overlaps the other, as in the examples of FIG. 4A-4C above. Typically, the detector panel and coordinate system is aligned with the radiation isocentre so that 2D images can be acquired with the patient in the same position during an irradiation sequence, even if the pulses are interlaced to enable best image quality. Optionally, the radiation delivery variables may be further updated or adjusted according to the results of the intrafraction image.

A computer-based system may be used for controlling or operating various parts of the systems, devices, methods and apparatuses disclosed herein. The computer-based system can be implemented in software, firmware and/or hardware and may comprise a computer-readable medium containing instructions that, when executed by a processor, cause the system to perform any of the methods described herein.

The above implementations have been described by way of example only, and the described implementations and arrangements are to be considered in all respects only as illustrative and not restrictive. It will be appreciated that variations of the described implementations and arrangements may be made without departing from the scope of the invention.

The invention claimed is:

1. A radiotherapy device comprising:
a source of therapeutic radiation; and
an imaging system, the imaging system comprising:
a source of imaging radiation; and
a detector;
wherein the imaging system is switchable between a first configuration and a second configuration, wherein, in the first configuration, the imaging system is configured to emit a beam of imaging radiation shaped for a first imaging modality toward the detector and, in the second configuration, the imaging system is configured to emit a beam of imaging radiation shaped for a second imaging modality toward the detector, wherein the detector has a shape formed by at least a first section and a second section, wherein the first section and the second section intersect with one another, wherein the first section is positioned for receiving the beam of imaging radiation for the first imaging modality, and wherein the second section is positioned for receiving the beam of imaging radiation for the second imaging modality, and wherein the detector comprises:

an array of tileable photodetectors each configured to provide a signal indicative of an intensity of imaging radiation incident thereon.

2. The radiotherapy device of claim 1, wherein the first imaging modality includes a computed tomography (CT) imaging and the second imaging modality includes a cone beam computed tomography (CBCT) imaging.

3. The radiotherapy device of claim 1, wherein the beam of imaging radiation shaped for the first imaging modality is fan-shaped, and the beam of imaging radiation shaped for the second imaging modality is cone-shaped.

4. The radiotherapy device of claim 1, wherein the first section and the second section intersect to define an intersection area which, when in use, receives imaging radiation when the imaging system is in either the first configuration or the second configuration.

5. The radiotherapy device of claim 1, wherein the first section and second section intersect one another such that the detector is one of cross-shaped, 'T'-shaped, or 'L'-shaped.

6. The radiotherapy device of claim 1, wherein the detector has a non-quadrilateral perimeter shape.

7. The radiotherapy device of claim 1, wherein the array of tileable photodetectors forms a shape having an outer perimeter that has more than four vertices.

8. The radiotherapy device of claim 1, wherein each tileable photodetector in the array comprises a direct conversion compound semiconductor sensor.

9. The radiotherapy device of claim 1, wherein the detector is a computed tomography CT imaging detector.

10. The radiotherapy device of claim 1, wherein the imaging system and source of therapeutic radiation are coupled to a rotatable gantry.

11. The radiotherapy device of claim 10, wherein the rotatable gantry is a ring gantry.

12. The radiotherapy device of claim 10, where the rotatable gantry is continuously rotatable.

13. The radiotherapy device of claim 10, wherein the source of therapeutic radiation is configured to emit radiation along a first axis and the source of imaging radiation is configured to emit radiation along a second axis, and wherein the first axis and second axis meet at a point defining a common isocentre for the source of therapeutic radiation and the imaging system.

14. The radiotherapy device of claim 13, wherein a rotation axis of the rotatable gantry passes through the common isocentre, in a direction which is perpendicular to both beam axes.

15. The radiotherapy device of claim 10, wherein the detector is located 45 degrees from a source direction of the source of therapeutic radiation.

16. A method of imaging using a radiotherapy device comprising:
a source of therapeutic radiation; and
an imaging system, the imaging system comprising a source of imaging radiation and a detector, wherein the imaging system is switchable between a first configuration and a second configuration, wherein, in the first configuration, the imaging system is configured to emit a beam of imaging radiation shaped for a first imaging modality toward the detector and, in the second configuration, the imaging system is configured to emit a beam of imaging radiation shaped for a second imaging modality toward the detector, wherein the detector has a shape formed by at least a first section and a second section, wherein the first section and the second section intersect with one another, wherein the first section is positioned for receiving the beam of imaging radiation for the first imaging modality, and wherein the second section is positioned for receiving the beam of imaging radiation for the second imaging modality, and wherein the detector comprises an array of tileable photodetectors each configured to provide a signal indicative of an intensity of imaging radiation incident thereon, the method comprising:
acquiring, according to the first imaging modality, a first image using the source of imaging radiation in the first configuration and a signal received from the first section of the detector;
switching the source of imaging radiation from the first configuration to the second configuration; and
acquiring, according to the second imaging modality, a second image using the source of imaging radiation in the second configuration and a second signal received from the second section of the detector.

17. The method of claim 16 wherein the first image is acquired prior to treatment, and wherein the second image is an intrafraction image.

18. The method of claim 16, the method further comprising:
updating one or more radiation delivery variables based on the first image; and
configuring the radiotherapy device to deliver treatment according to the updated radiation delivery variables.

19. A non-transitory computer-readable medium containing instructions that, when executed by a processor of a computing device controlling a radiotherapy device, cause the processor to perform operations, wherein the radiotherapy device comprises:
a source of therapeutic radiation; and
an imaging system comprising:
a source of imaging radiation; and
a detector, wherein the imaging system is switchable between a first configuration and a second configuration, wherein, in the first configuration, the imaging system is configured to emit a beam of imaging radiation shaped for a first imaging modality toward the detector, and wherein, in the second configuration, the imaging system is configured to emit a beam of imaging radiation shaped for a second imaging modality toward the detector and wherein the detector has a shape formed by at least a first section and a second section, wherein the first section and the second section intersect with one another, wherein the first section is positioned for receiving the beam of imaging radiation for the first imaging modality, and wherein the second section is positioned for receiving the beam of imaging radiation for the second imaging modality;

the operations comprising:
  acquiring, according to the first imaging modality, a first image using the source of imaging radiation in the first configuration and a signal received from the first section of the detector;
  switching the source of imaging radiation from the first configuration to the second configuration; and
  acquiring, according to the second imaging modality, a second image using the source of imaging radiation in the second configuration and a signal received from the second section of the detector, wherein the detector comprises:
  an array of tileable photodetectors each configured to provide a signal indicative of an intensity of imaging radiation incident thereon.

* * * * *